US009458740B2

(12) United States Patent
Hirson et al.

(10) Patent No.: US 9,458,740 B2
(45) Date of Patent: Oct. 4, 2016

(54) METHOD FOR SEQUESTERING HEAVY METAL PARTICULATES USING $H_2O$, $CO_2$, $O_2$, AND A SOURCE OF PARTICULATES

(71) Applicant: POWERDYNE, INC., Newport Beach, CA (US)

(72) Inventors: Geoffrey Hirson, Newport Beach, CA (US); Gus F. Shouse, Newport Beach, CA (US)

(73) Assignee: Powerdyne, Inc., Newport Beach, CA (US)

( * ) Notice: Subject to any disclaimer, the term of this patent is extended or adjusted under 35 U.S.C. 154(b) by 0 days.

(21) Appl. No.: 14/426,261

(22) PCT Filed: Sep. 5, 2013

(86) PCT No.: PCT/US2013/058331
§ 371 (c)(1),
(2) Date: Mar. 5, 2015

(87) PCT Pub. No.: WO2014/039723
PCT Pub. Date: Mar. 13, 2014

(65) Prior Publication Data

US 2015/0209693 A1 Jul. 30, 2015

Related U.S. Application Data

(60) Provisional application No. 61/697,148, filed on Sep. 5, 2012.

(51) Int. Cl.
*B01D 21/01* (2006.01)
*F01K 25/06* (2006.01)
(Continued)

(52) U.S. Cl.
CPC ........... *F01K 25/06* (2013.01); *B01D 21/0009* (2013.01); *B01D 21/01* (2013.01);
(Continued)

(58) Field of Classification Search
CPC ............................... H05H 1/46; Y10S 588/90
See application file for complete search history.

(56) References Cited

U.S. PATENT DOCUMENTS

| | | | |
|---|---|---|---|
| 1,746,464 | A | 2/1930 | Fischer et al. |
| 3,979,205 | A | 9/1976 | Wanzenberg |

(Continued)

FOREIGN PATENT DOCUMENTS

| | | | |
|---|---|---|---|
| CA | 2379892 | A1 | 2/2001 |
| CN | 1268550 | A | 10/2000 |

(Continued)

OTHER PUBLICATIONS

International Search Report and Written Opinion dated Jul. 28, 2014 for International Application No. PCT/US2014/024606.

(Continued)

*Primary Examiner* — Walter D Griffin
*Assistant Examiner* — Cameron J Allen
(74) *Attorney, Agent, or Firm* — Pepper Hamilton LLP

(57) ABSTRACT

Methods of sequestering toxin particulates are described herein. In a primary processing chamber, a carbon source of toxin particulates may be combined with plasma from three plasma torches to form a first fluid mixture and vitrified toxin residue. Each torch may have a working gas including oxygen gas, water vapor, and carbon dioxide gas. The vitrified toxin residue is removed. The first fluid mixture may be cooled in a first heat exchange device to form a second fluid mixture. The second fluid mixture may contact a wet scrubber. The final product from the wet scrubber may be used as a fuel product.

21 Claims, 3 Drawing Sheets

(51) Int. Cl.

| | |
|---|---|
| ***B01D 21/00*** | (2006.01) |
| ***B01J 12/00*** | (2006.01) |
| ***B01J 19/08*** | (2006.01) |
| ***B09B 3/00*** | (2006.01) |
| ***C01B 3/02*** | (2006.01) |
| ***C01B 3/04*** | (2006.01) |
| ***C01B 3/12*** | (2006.01) |
| ***C07C 1/04*** | (2006.01) |
| ***C10G 2/00*** | (2006.01) |
| ***C10J 3/00*** | (2006.01) |
| ***C10L 1/06*** | (2006.01) |
| ***C10L 1/08*** | (2006.01) |
| ***F02C 1/05*** | (2006.01) |
| ***H05H 1/34*** | (2006.01) |
| ***H05H 1/42*** | (2006.01) |
| ***H05H 1/44*** | (2006.01) |

(52) U.S. Cl.

CPC ........... *B01J 12/002* (2013.01); *B01J 19/088* (2013.01); *B09B 3/005* (2013.01); *C01B 3/02* (2013.01); *C01B 3/042* (2013.01); *C01B 3/12* (2013.01); *C07C 1/04* (2013.01); *C10G 2/32* (2013.01); *C10J 3/00* (2013.01); *C10L 1/06* (2013.01); *C10L 1/08* (2013.01); *F02C 1/05* (2013.01); *H05H 1/34* (2013.01); *H05H 1/42* (2013.01); *H05H 1/44* (2013.01); *B01J 2219/0809* (2013.01); *B01J 2219/0815* (2013.01); *B01J 2219/0875* (2013.01); *B01J 2219/0877* (2013.01); *B01J 2219/0898* (2013.01); *C01B 2203/062* (2013.01); *C01B 2203/0861* (2013.01); *C10J 2300/1238* (2013.01); *C10J 2300/1671* (2013.01); *C10J 2300/1675* (2013.01); *C10L 2200/043* (2013.01); *C10L 2200/0415* (2013.01); *C10L 2200/0423* (2013.01); *C10L 2200/0446* (2013.01); *C10L 2290/38* (2013.01); *C10L 2290/42* (2013.01); *Y02E 50/32* (2013.01); *Y02E 60/364* (2013.01); *Y02P 20/13* (2015.11)

(56) References Cited

U.S. PATENT DOCUMENTS 4,466,807 A 8/1984 Santen et al.
4,508,040 A 4/1985 Santen et al.
4,591,428 A 5/1986 Pronk
4,770,109 A 9/1988 Schlienger
4,831,944 A 5/1989 Durand et al.
4,845,334 A 7/1989 Stocks et al.
4,898,748 A 2/1990 Kruger, Jr.
5,046,144 A 9/1991 Jensen
5,107,517 A 4/1992 Lauren
5,136,137 A 8/1992 Schlienger
5,138,959 A 8/1992 Kulkarni
5,288,969 A 2/1994 Wong et al.
5,301,620 A 4/1994 Nagel et al.
5,319,176 A * 6/1994 Alvi ........................ A62D 3/19 110/236
5,493,578 A 2/1996 Fukusaki et al.
5,534,659 A 7/1996 Springer et al.
5,541,386 A 7/1996 Alvi et al.
5,544,597 A 8/1996 Camacho
5,611,947 A 3/1997 Vavruska
5,634,414 A 6/1997 Camacho
5,666,891 A 9/1997 Titus et al.
5,673,635 A 10/1997 Fowler
5,725,616 A 3/1998 Lynum et al.
5,798,496 A 8/1998 Eckhoff et al.
5,868,027 A 2/1999 Norton et al.
5,935,293 A 8/1999 Detering et al.
5,958,264 A 9/1999 Tsantrizos et al.
6,127,645 A 10/2000 Titus et al.
6,153,852 A 11/2000 Blutke et al.
6,173,002 B1 1/2001 Robert
6,187,226 B1 2/2001 Detering et al.
6,215,678 B1 4/2001 Titus et al.
6,289,851 B1 9/2001 Rabovitser et al.
6,355,904 B1 3/2002 Batdorf et al.
6,372,156 B1 4/2002 Kong et al.
6,375,832 B1 4/2002 Eliasson et al.
6,505,567 B1 1/2003 Anderson et al.
6,524,538 B2 2/2003 Barankova et al.
6,552,295 B2 4/2003 Markunas et al.
6,810,821 B2 11/2004 Chan
6,821,500 B2 11/2004 Fincke et al.
6,874,434 B1 4/2005 Bigelow et al.
6,971,323 B2 12/2005 Capote et al.
6,976,362 B2 12/2005 Sheppard et al.
6,987,792 B2 1/2006 Do et al.
7,070,634 B1 7/2006 Wang
7,097,675 B2 8/2006 Detering et al.
7,279,655 B2 10/2007 Blutke et al.
7,335,320 B2 2/2008 Kingdig et al.
7,384,619 B2 6/2008 Bar-Gadda
7,576,296 B2 8/2009 Fincke et al.
7,622,693 B2 11/2009 Foret
7,674,443 B1 3/2010 Davis
7,832,344 B2 11/2010 Capote et al.
7,845,411 B2 12/2010 Vinegar et al.
7,981,371 B2 7/2011 Meillot et al.
8,129,654 B2 3/2012 Lee et al.
8,168,128 B2 5/2012 Seeley et al.
8,199,790 B2 6/2012 Vera
8,216,433 B2 7/2012 Yonesu
8,252,244 B2 8/2012 Capote et al.
8,268,094 B2 9/2012 Zurecki et al.
8,277,631 B2 10/2012 Eastman et al.
8,303,916 B2 11/2012 Collins et al.
8,324,523 B2 12/2012 Foret
8,357,873 B2 1/2013 Foret
8,367,005 B2 2/2013 Ikeda et al.
8,475,551 B2 7/2013 Tsangaris et al.
8,518,162 B2 8/2013 Smith et al.
8,519,354 B2 8/2013 Charipar et al.
2002/0000085 A1 1/2002 Hall et al.
2002/0040889 A1 * 4/2002 Markunas ................ H05H 1/46 219/121.36
2002/0151604 A1 10/2002 Detering et al.
2003/0029796 A1 2/2003 Maekawa
2003/0065042 A1 4/2003 Shaw
2003/0209174 A1 11/2003 Chan
2004/0134517 A1 7/2004 Clark
2004/0251241 A1 12/2004 Blutke et al.
2006/0053791 A1 3/2006 Prentice, III
2006/0060464 A1 3/2006 Chang
2006/0112639 A1 6/2006 Nick et al.
2006/0201157 A1 9/2006 Villalobos
2006/0233699 A1 10/2006 Mills
2007/0017228 A1 1/2007 Surma
2007/0186474 A1 8/2007 Rabovitser et al.
2007/0253874 A1 11/2007 Foret
2007/0266633 A1 11/2007 Tsangaris et al.
2007/0267289 A1 11/2007 Jabs et al.
2007/0272131 A1 11/2007 Carabin et al.
2008/0041829 A1 2/2008 Blutke et al.
2008/0083701 A1 4/2008 Shao et al.
2008/0147241 A1 6/2008 Tsangaris et al.
2008/0184621 A1 8/2008 Clark
2008/0202028 A1 8/2008 Tsangaris et al.
2008/0209807 A1 9/2008 Tsangaris et al.
2008/0222956 A1 9/2008 Tsangaris et al.
2008/0223047 A1 9/2008 Oliver
2008/0277265 A1 11/2008 Tsangaris et al.
2008/0283153 A1 11/2008 Zurecki et al.
2008/0283411 A1 11/2008 Eastman et al.
2008/0290322 A1 11/2008 Hederer et al.
2009/0038958 A1 2/2009 Coyle et al.
2009/0133407 A1 5/2009 Sawyer
2009/0183430 A1 7/2009 Schubert et al.
2009/0188127 A1 7/2009 Gorbell et al.

(56) References Cited

U.S. PATENT DOCUMENTS

| | | | |
|---|---|---|---|
| 2009/0307975 | A1 | 12/2009 | Wolf |
| 2010/0050654 | A1 | 3/2010 | Chiu et al. |
| 2010/0065781 | A1 | 3/2010 | Brothier |
| 2010/0167139 | A1 | 7/2010 | Gattis et al. |
| 2010/0229522 | A1 | 9/2010 | Kingzett |
| 2010/0298449 | A1 | 11/2010 | Rojey |
| 2011/0067376 | A1 | 3/2011 | Tompkins et al. |
| 2011/0162523 | A1 | 7/2011 | Fabbri et al. |
| 2011/0162958 | A1 | 7/2011 | Cho et al. |
| 2011/0201700 | A1 | 8/2011 | Lucas et al. |
| 2011/0212012 | A1 | 9/2011 | McAlister |
| 2011/0265698 | A1 | 11/2011 | Hirson et al. |
| 2011/0286893 | A1 | 11/2011 | Zimmerman et al. |
| 2012/0000115 | A1 | 1/2012 | Shastri |
| 2012/0032452 | A1 | 2/2012 | Kuku |
| 2012/0070347 | A1 | 3/2012 | Bacon et al. |
| 2012/0090985 | A1 | 4/2012 | Rabinovich et al. |
| 2012/0114877 | A1 | 5/2012 | Lee |
| 2012/0121468 | A1 | 5/2012 | Tsangaris et al. |
| 2012/0291436 | A1 | 11/2012 | Hirson et al. |
| 2013/0200624 | A1 | 8/2013 | Hirson et al. |
| 2013/0300121 | A1 | 11/2013 | Ali et al. |

FOREIGN PATENT DOCUMENTS

| | | | |
|---|---|---|---|
| CN | 1810938 | A | 8/2006 |
| EP | 1270508 | A1 | 1/2003 |
| GB | 573982 | | 12/1945 |
| WO | WO 2005/005009 | A2 | 1/2005 |
| WO | WO 2008/130260 | A1 | 10/2008 |
| WO | WO 2009/156761 | A2 | 12/2009 |
| WO | WO 2010/056462 | A1 | 5/2010 |
| WO | WO 2011/091327 | A1 | 7/2011 |
| WO | WO 2011/140080 | A2 | 11/2011 |
| WO | WO 2012/039751 | A2 | 3/2012 |
| WO | WO 2012/064936 | A1 | 5/2012 |
| WO | WO 2012/077198 | A1 | 6/2012 |
| WO | WO 2012/158797 | A1 | 11/2012 |
| WO | WO 2012/177666 | A1 | 12/2012 |

OTHER PUBLICATIONS

International Search Report and Written Opinion dated Jan. 17, 2014 for International Application No. PCT/US2013/058287.

International Search Report and Written Opinion dated Feb. 7, 2014 for International Application No. PCT/US2013/058301.

International Search Report and Written Opinion dated Dec. 12, 2013 for International Application No. PCT/US2013/058305.

International Search Report and Written Opinion dated Feb. 7, 2014 for International Application No. PCT/US2013/058315.

International Search Report and Written Opinion dated Feb. 7, 2014 for International Application No. PCT/US2013/058326.

International Search Report and Written Opinion dated Jan. 22, 2014 for International Application No. PCT/US2013/058331.

International Search Report and Written Opinion dated Jan. 16, 2014 for International Application No. PCT/US2013/058335.

Plasco Group, "How is Plasco Different?," http://www:plascoenergygroup.com/our-solution/how-is-plasco-different/, retrieved from web Jul. 5, 2011.

Schuey et al., "LLW Processing and Operational Experience Using a Plasma ARC Centrifugal Treatment (PACT) System," *WM'06 Conference*, Feb. 26-Mar. 2, 2006, Tucson, AZ.

Urashima et al., "Removal of Volatile Organic Compounds from Air Streams and Industrial Flue Gases by Non-Thermal Plasma Technology," *IEEE Transactions on Dielectrics and Electrical Insulation*, Oct. 2000, 7(5):602-614.

International Search Report and Written Opinion dated Feb. 24, 2015 for International Application No. PCT/US2014/069342.

"C-17 flight uses synthetic fuel blend," (Oct. 25, 2007), Wright-Patterson Air Force Base, Retrieved Feb. 7, 2008, http://www.wpafb.af.mil/news/story.asp?id=123073170.

Fairley, Peter, "Growing Biofuels," (Nov. 23, 2005), MIT Technology Review, http://www.technologyreview.com/news/404941/growing-biofuels/.

"Governor Rendell leads with innovative solution to help address PA energy needs," State of Pennsylvania. Archived from original on Dec. 11, 2008, http://web.archive.org/web/20081211180710/http:/www.state.pa.us/papower/cwp/view.asp?Q=446127&A=11.

Jamieson et al., "Keeping the Options Open", *Petroleum Economist*, Retrieved LNG 2012.

Krauss, Clifford, "South African Company to Build U.S. Plant to Convert Gas to Liquid Fuels," (Dec. 3, 2012), *New York Times*, http://www.nytimes.com/2012/12/04/business/energy-environment/sasol-plans-first-gas-to-liquids-plant-in-us.html?_r=l.

Lane, Jim, "Little Big Tech: Can Fischer-Tropsch technology work at smaller scale?" (Nov. 20, 2012), *Biofuels Digest*, http://www.biofuelsdigest.com/bdigest/2012/11/20/little-big-tech-can-fischer-tropsch-technology-work-at-smaller-scale/.

"PetroSA Wins Innovation Award," SouthAfrica.info, (Oct. 10, 2008), Retrieved Dec. 18, 2012, http://www.southafrica.info/business/trends/innovations/petrosa-101008.htm.

"PetroSA technology ready for next stage," Businessday.co.za, (May 10, 2011) Retrieved Jun. 5, 2013, http://www.bdlive.co.za/articles/2011/05/10/petrosa-technology-ready-for-next-stage.

Pitt, Anthea, "Linc gears up for Chinchilla GTL," (Nov. 28, 2012), Upstreamonline.com, http://www.upstreamonline.com/live/article1149671.ece?print=preview.

"Schweitzer wants to convert Otter Creek coal into liquid fuel," (Aug. 2, 2005), *Billings Gazette*, Archived from original on Jan. 1, 2009.

Smedley, Mark, "Small GTL's Market Reach as Great as Opec's, UK Firm Says," *World Gas Intelligence*, Retrieved Dec. 19, 2012, http://www.oxfordcatalyst.com/press/egs/world_gas_intelligence_121219.pdf.

Steynberg et al., "Clean Coal Conversion Options Using Fischer-Tropsch Technology," (2003), Fuel Chemistry Division Preprints, 48(1); 459-461.

"UPM-Kymmene says to establish beachhead in biodesel market," NewsRoom Finland. Archived from original on Mar. 17, 2007, http://web.archive.org/web/20070317104947/http:/newsroom.finland.fi/stt/showarticle.asp?intNWSAID=14179&group=Business.

Supplemental European Search Report for EP13836174 dated Mar. 31, 2016.

Supplemental European Search Report for EP 13835933 dated Mar. 31, 2016.

Supplemental European Search Report for EP 13834468 dated Mar. 31, 2016.

Supplemental European Search Report for EP 13834969 dated Apr. 1, 2016.

Supplemental European Search Report for EP 13835425 dated Apr. 1, 2016.

Supplemental European Search Report for EP 13835534 dated Apr. 11, 2016.

Supplemental European Search Report for EP 13835723 dated Mar. 31, 2016.

* cited by examiner

METHOD FOR SEQUESTERING HEAVY METAL PARTICULATES USING $H_2O$, $CO_2$, $O_2$, AND A SOURCE OF PARTICULATES

CLAIM OF PRIORITY

This application is a national phase application under 35 U.S.C. §371 of International Application No. PCT/US2013/058331, entitled "Method for Sequestering Heavy Metal Particulates Using $H_2O$, $CO_2$, $O_2$, and a Source of Particulates," and filed Sep. 5, 2013, which claims the benefit of and priority to U.S. Provisional Patent Application No. 61/697,148, entitled "Methods for Generating Fuel Materials and Power, and Sequestering Toxins Using Plasma Sources," which was filed on Sep. 5, 2012. The aforementioned applications are incorporated by reference herein in their entireties and for all purposes.

BACKGROUND

Various materials may be found to be contaminated with heavy metal particulates. For example, heavy metal particulates may be found in mine tailings after extraction of minerals from ore mining Heavy metals such as, arsenic, uranium, lead, iron, copper, and zinc are commonly found in mine tailings. Heavy metals may leach out of these various materials into the environment and may be harmful or toxic. It may be necessary to remove heavy metal particulates from various materials.

It is therefore desirable to develop high efficiency methods for sequestering heavy metal particulates from various materials.

SUMMARY

In an embodiment, a method of sequestering toxin particulates may include providing a first working fluid, exposing the first working fluid to a first high voltage electric field to produce a first fluid plasma, providing a second working fluid, exposing the second working fluid to a second high voltage electric field to produce a second fluid plasma, providing a third working fluid, exposing the third working fluid to a third high voltage electric field to produce a third fluid plasma, providing an amount of toxin particulates, contacting the toxin particulates with the third fluid plasma, the second fluid plasma, and the first fluid plasma within a primary processing chamber to form a first fluid mixture and vitrified toxin residue, removing the vitrified toxin residue, transporting the first fluid mixture to a first heat exchange device, cooling the first fluid mixture using the first heat exchange device to form a second fluid mixture, and transporting the second fluid mixture to a wet scrubber.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The following terms shall have, for the purposes of this application, the respective meanings set forth below.

As used herein, a toxin particulate may generally include any composition of matter that is a poisonous substance. Particular toxin particulates that may be sequestered include mine tailings, pulverized mine tailings, heavy metal particulates, or a blend of mine tailings and heavy metal particulates.

As used herein, vitrified toxin residue may generally include any composition of toxin matter that is transformed from a source of toxin particulates through heat fusion after removal of useful substances. Particular vitrified toxin residue includes heavy metal particulates.

Methods described herein may be used to generate various gaseous or liquid fuel materials after removal of heavy metal particulates. In the various embodiments described herein, a method of sequestering toxin particulates may include providing a first working fluid, exposing the first working fluid to a first high voltage electric field to produce a first fluid plasma, providing a second working fluid, exposing the second working fluid to a second high voltage electric field to produce a second fluid plasma, providing a third working fluid, exposing the third working fluid to a third high voltage electric field to produce a third fluid plasma, providing an amount of toxin particulates, contacting the toxin particulates with the third fluid plasma, the second fluid plasma, and the first fluid plasma within a primary processing chamber to form a first fluid mixture and vitrified toxin residue, removing the vitrified toxin residue, transporting the first fluid mixture to a first heat exchange device, cooling the first fluid mixture using the first heat exchange device to form a second fluid mixture, and transporting the second fluid mixture to a wet scrubber.

Figure 1A:
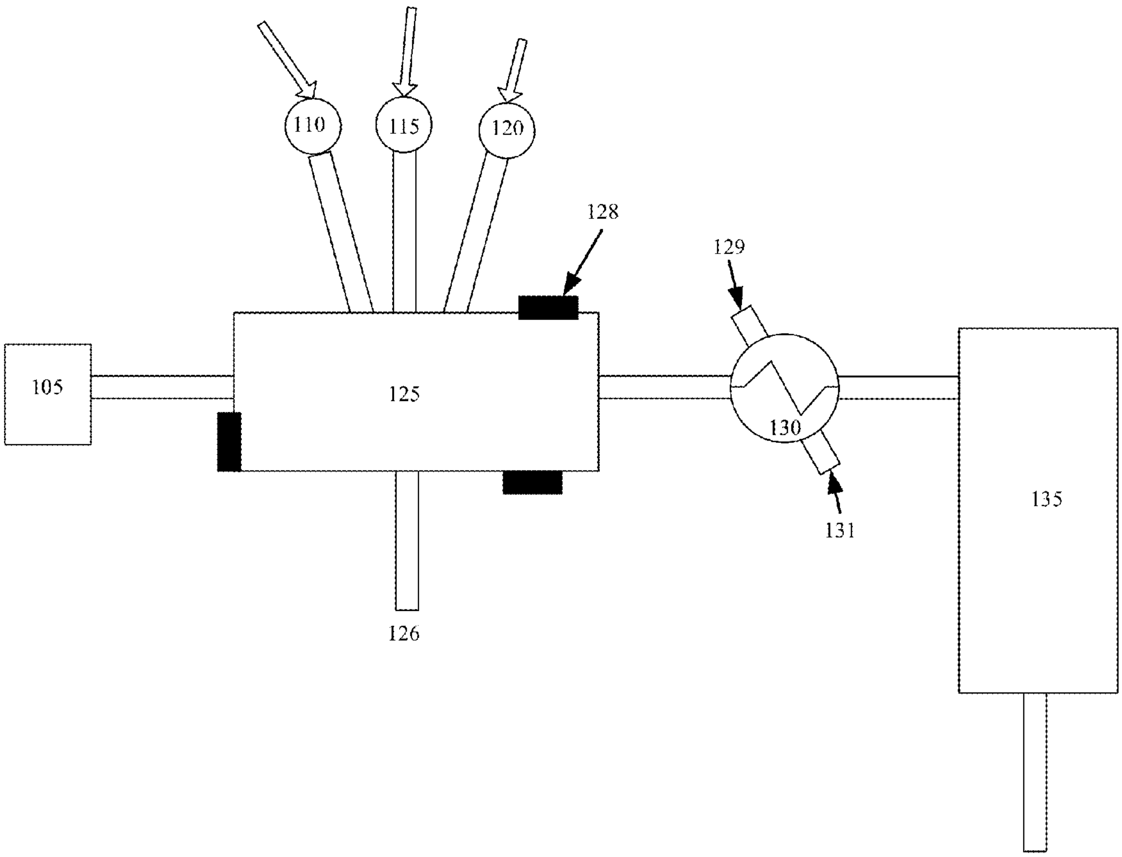
FIG. 1A depicts a block diagram of a system for sequestering heavy metal particulates using $H_2O$, $CO_2$, $O_2$, and a source of toxin particulates according to an embodiment.

FIG. 1A depicts a block diagram of a system for sequestering heavy metal particulates using $H_2O$, $CO_2$, $O_2$, and a source of toxin particulates according to an embodiment. The system may generally include a supply of carbon source to provide toxin particulates 105, one or more plasma sources, which may include a first high voltage electric field generator 110, a second high voltage electric field generator 115, and a third high voltage electric field generator 120, a primary processing chamber (PPC) 125, a coolant addition device 128, a residue exit port 126, a first water input port 129, a first heat exchange device 130, a first output port 132, and a scrubber 135.

Figure 2:
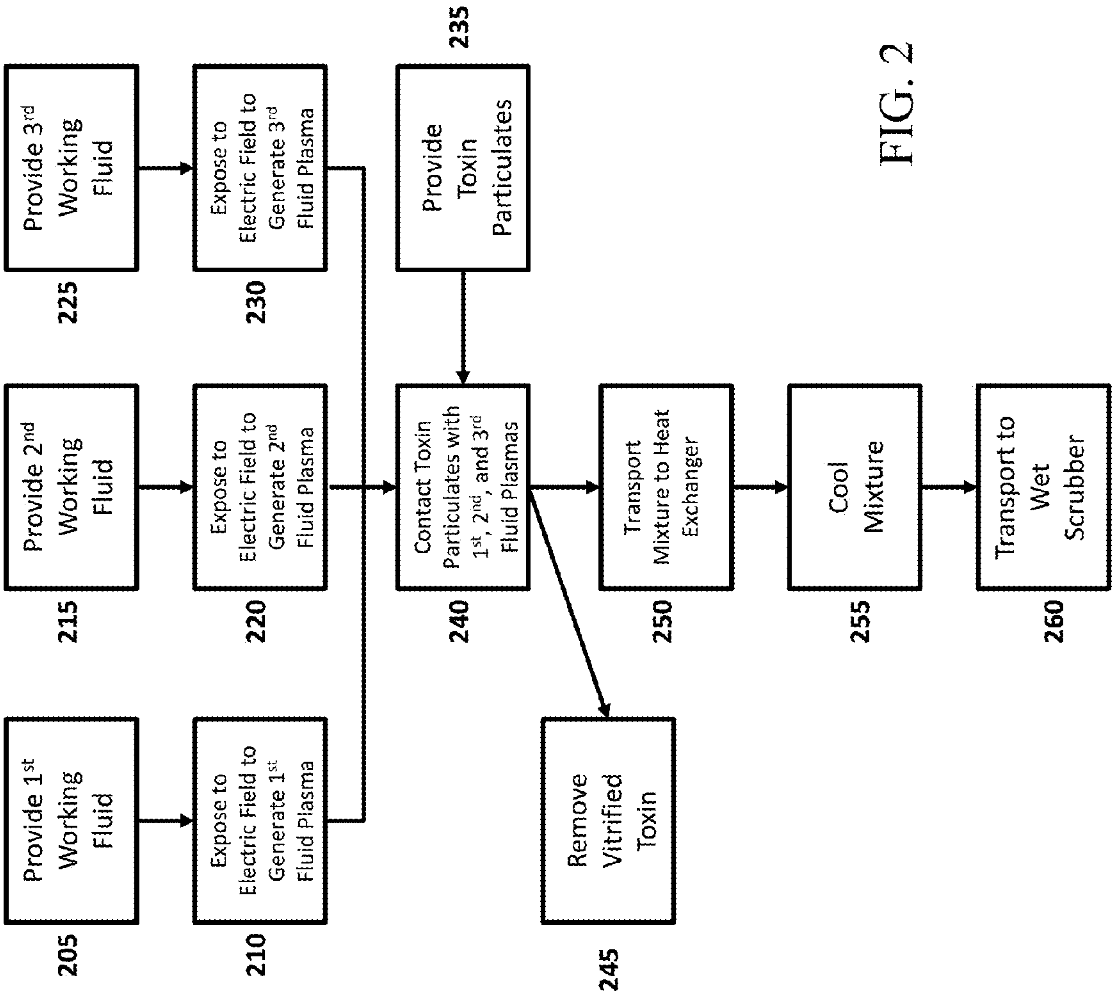
FIG. 2 depicts a flow diagram of an illustrative method of sequestering toxin particulates according to an embodiment.

FIG. 2 depicts a flow diagram of an illustrative method of sequestering toxin particulates according to an embodiment. The method may include providing 205 a first working fluid, providing 215 a second working fluid, and providing 225 a third working fluid. In one non-limiting embodiment, the first working fluid may be oxygen gas ($O_2$), the second working fluid may be water vapor ($H_2O$), and the third working fluid may be carbon dioxide gas ($CO_2$). The first working fluid may be exposed 210 to a first high-voltage electric field to generate a first fluid plasma. The second working fluid may be exposed 220 to a second high-voltage electric field to generate a second fluid plasma. The third working fluid may be exposed 230 to a third high-voltage electric field to generate a third fluid plasma. A carbon source for toxin particulates may be provided 235, and then contacted 240 with the first fluid plasma, second fluid plasma, and third fluid plasma. A first fluid mixture and vitrified toxin residue is produced within the PPC. The vitrified toxin residue may be removed 245 and the first fluid mixture may then be transported 250 to a first heat exchange device. The mixture may then be cooled 255, and then transported 260 to a wet scrubber.

In some embodiments, a carbon source 105 that provides 235 toxin particulates may include mine tailings, pulverized mine tailings, mine dumps, culm dumps, slimes, tails, refuse, leach residue, slickens, ground rock, mine process effluents, ore process refuse, dross, earth extractions, heavy metal particulates, or combinations thereof. In other embodiments, the carbon source 105 may include one or more binding particulates. The binding particulates may include silicates, clays, iron oxide clays, aluminum oxide clays, allophane clays, humus, or combinations thereof.

The primary processing chamber (PPC) 120 as used herein may generally refer to any chamber that is capable of withstanding one or more processing conditions, such as temperature, pressure, corrosion, and the like, under which the combustion of working fluid in the presence of, for example, carbon dioxide, oxygen, and water takes place. In some embodiments, the PPC 120 may be incorporated with the one or more high-voltage electric fields generators 110, 115, 120. In some embodiments, the PPC may include one or more inlets for receiving plasma from the various high voltage electric field generators 110, 115, 120, and at least one outlet for discharging a plasma mixture, as described in greater detail herein. An illustrative PPC 120 may be a plasma arc centrifugal treatment (PACT) system available from Retech Systems, LLC, (Ukiah, Calif.) which, includes at least one plasma torch.

Figure 1B:
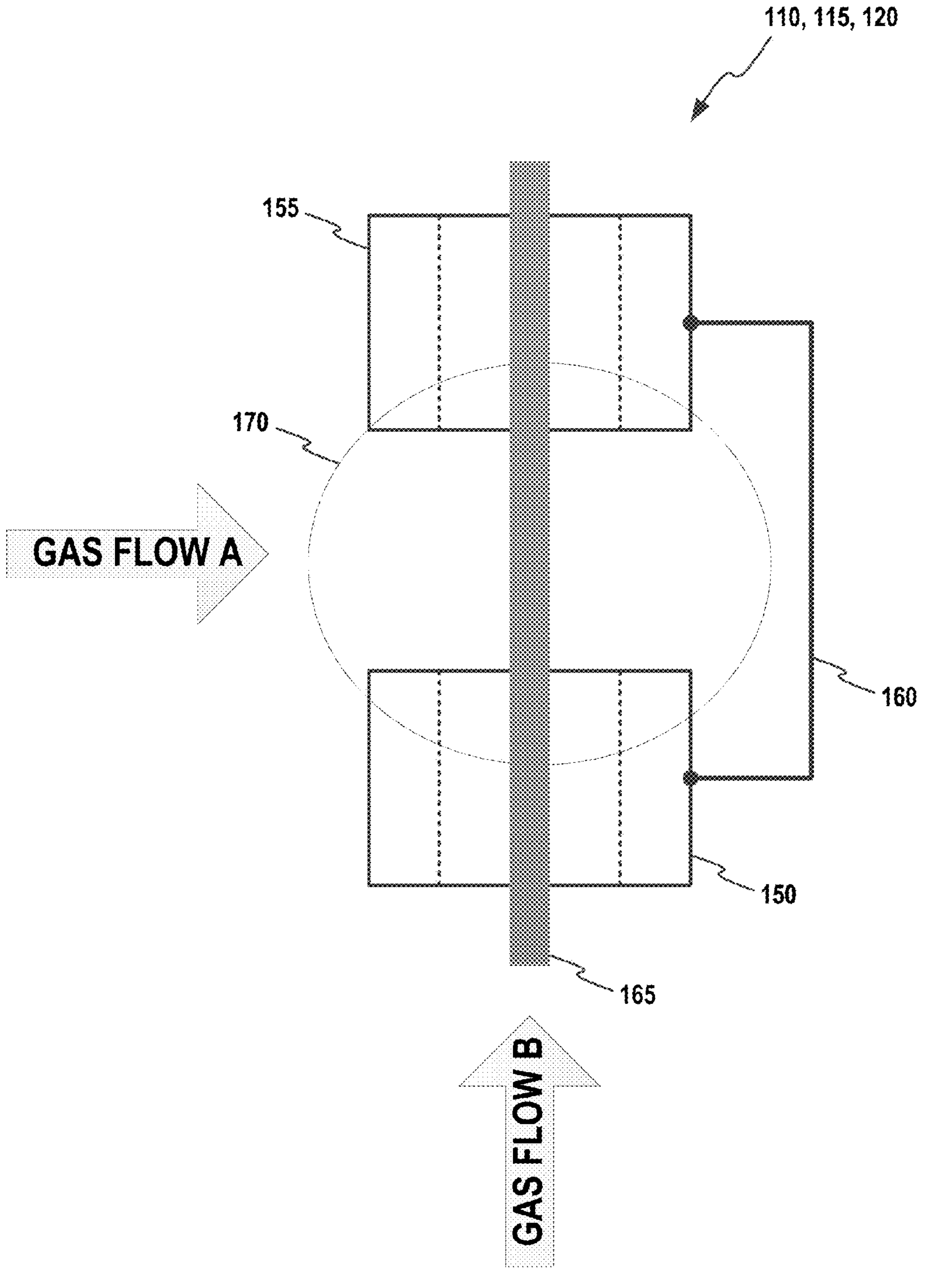
FIG. 1B depicts a graphical diagram of an electric field generator according to an embodiment.

Each of the one or more high-voltage electric field generators 110, 115, 120 may generally be any of various components that may be used to generate a high voltage potential. FIG. 1B depicts a graphical diagram of an electric field generator according to an embodiment. Thus, as shown in FIG. 1B, each of the one or more high-voltage electric field generators 110, 115, 120 may have at least one anode surface 150, at least one cathode surface 155, and an electric potential 160 between the anode surface and the cathode surface. As a result, a magnetic field 165 and an electric field 170 may be generated when the electric potential 160 is applied between the at least one anode surface 150 and the at least one cathode surface 155. In some embodiments, a flow of gas, as described in greater detail herein and indicated by the horizontal arrow, may be substantially perpendicular to the magnetic field 165. In other embodiments, the flow of gas, as indicated by the vertical arrow, may be substantially parallel to the magnetic field 165. The magnetic field 165 and the electric field 170 may each have an effect on gas that flows through a gap between the anode surface 150 and the cathode surface 155. In a non-limiting example, the electric field 170 may stabilize the gas and/or ionize the gas. In another non-limiting example, the magnetic field 165 may alter a spin and/or a velocity of the gas.

Within a PPC 125, a first fluid plasma, a second fluid plasma, and a third fluid plasma may be introduced. The first fluid plasma, second fluid plasma, and third fluid plasma may be contained within the PPC. The first fluid plasma may be generated by exposing 210 a first working fluid to a first high voltage electric field, generated by a first high voltage electric field generator 110, such as a first plasma torch, the second fluid plasma may be generated by exposing 220 a second working fluid to a second high voltage electric field, generated by a second high voltage electric field generator 115, such as a second plasma torch, and the third fluid plasma may be generated by exposing 230 a third working fluid to a third high voltage electric field, generated by a third high voltage electric field generator 120, such as a third plasma torch. A plasma torch, as used herein, may generally include any device capable of generating a directed flow of plasma. Illustrative plasma torches may include, but are not limited to, ionized gas plasma generating systems, such as Inductively Coupled Plasma, Transferred Arc DC Plasma, and Non-Transferred Arc DC Plasma. As uses herein, the terms "torch" or "torches" refer to plasma torches. The torches may be capable of reaching temperatures ranging of up to about 10,000° F. to about 20,000° F. (about 5,540° C. to about 11,090° C.), or more. Each plasma torch may be a portion of a plasma reactor, which is generally a combination of a plasma torch and a reaction vessel with which the plasma torch is used.

In some embodiments, the first working fluid may be oxygen gas ($O_2$), the second working fluid may be water vapor ($H_2O$), and the third working fluid may be carbon dioxide gas ($CO_2$). In some embodiments, the first fluid plasma, second fluid plasma, and third fluid plasma may each attain a temperature of about 20,000° C. at the output of their respective plasma torches. In other embodiments, the second working fluid may also include carbon dioxide. In further embodiments, the third working fluid may include an amount of carbon dioxide obtained from the second fluid mixture. In yet further embodiments, the second fluid mixture may include toxic material silicates, toxic material carbonates, vitreous compositions including the toxic materials, or combinations thereof.

It may be appreciated that the $O_2$, $H_2O$, and $CO_2$ contained within the PPC 125 may be used as working fluids for their respective plasma torches. Thus, each gas may be exposed (210, 220, 230) to a high voltage electric field. As a result of exposure (210, 220, 230) to such fields, the gases may be reduced to free radical species (as examples, for $H_2O$, these may include the hydroxyl radical OH*, and for $O_2$ these may include the superoxide anion radical $O2^{*-}$) in addition to ionized species (for $O_2$, these may include $O^-$, $O_2^-$, $O_2^+$, and $O^+$). The types and amounts of reactive species created by exposure of the gases to high voltage electric fields may differ from those generated by exposure of the gases to heat alone.

In one non-limiting example of the method, exposing 210 the first working fluid to a first high voltage electric field may include providing an anode surface and a cathode surface separated by a distance to create a gap between the two surfaces. The distance may generally be selected such that (for the electrical voltage selected), the electrical field is about 0.3 kV/cm to about 8.0 kV/cm, including about 0.3 kV/cm, about 0.3149 kV/cm, about 0.5 kV/cm, about 0.75 kV/cm, about 1.0 kV/cm, about 1.25 kV/cm, about 1.5 kV/cm, about 1.574 kV/cm, about 2.0 kV/cm, about 2.5 kV/cm, about 3.0 kV/cm, about 3.149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints).

A first high voltage electric potential may be induced between the anode surface and the cathode surface, and the first working fluid may be induced to traverse the gap between the two surfaces. In one non-limiting embodiment, the first high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60 kV, or any value or range between any two of these values (including endpoints). In an embodiment, a voltage between the anode surface and the cathode surface (which is 0.3175 cm) is 2.4 kV, thereby resulting in an electrical field of about 7.559 kV/cm. In another non-limiting embodiment, the first high voltage electric potential may be an AC potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the first high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

In another non-limiting example of the method, exposing 220 the second working fluid to a second high voltage electric field may include providing an anode surface and a cathode surface separated by a distance to create a gap between the two surfaces. The distance may generally be selected such that (for the electrical voltage selected), the electrical field is about 0.3 kV/cm to about 8.0 kV/cm, including about 0.3 kV/cm, about 0.3149 kV/cm, about 0.5 kV/cm, about 0.75 kV/cm, about 1.0 kV/cm, about 1.25 kV/cm, about 1.5 kV/cm, about 1.574 kV/cm, about 2.0 kV/cm, about 2.5 kV/cm, about 3.0 kV/cm, about 3.149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints).

A second high voltage electric potential may be induced between the anode surface and the cathode surface, and the second working fluid may be induced to traverse the gap between the two surfaces. In one non-limiting embodiment, the second high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60 kV, or any value or range between any two of these values (including endpoints). In an embodiment, a voltage between the anode surface and the cathode surface (which is 0.3175 cm) is 2.4 kV, thereby resulting in an electrical field of about 7.559 kV/cm. In another non-limiting embodiment, the second high voltage electric potential may be an AC potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the second high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

In another non-limiting example of the method, exposing 230 the third working fluid to a third high voltage electric field may include providing an anode surface and a cathode surface separated by a distance to create a gap between the two surfaces. The distance may generally be selected such that (for the electrical voltage selected), the electrical field is about 0.3 kV/cm to about 8.0 kV/cm, including about 0.3 kV/cm, about 0.3149 kV/cm, about 0.5 kV/cm, about 0.75 kV/cm, about 1.0 kV/cm, about 1.25 kV/cm, about 1.5 kV/cm, about 1.574 kV/cm, about 2.0 kV/cm, about 2.5 kV/cm, about 3.0 kV/cm, about 3.149 kV/cm, about 3.5 kV/cm, about 4.0 kV/cm, about 4.5 kV/cm, about 5.0 kV/cm, about 5.5 kV/cm, about 6.0 kV/cm, about 6.5 kV/cm, about 7.0 kV/cm, about 7.5 kV/cm, about 7.559 kV/cm, about 8.0 kV/cm, or any value or range between any two of these values (including endpoints). Illustrative distances may be about 0.15 cm to about 0.65 cm, including about 0.15 cm, about 0.20 cm, about 0.25 cm, about 0.30 cm, about 0.3175 cm, about 0.35 cm, about 0.40 cm, about 0.45 cm, about 0.50 cm, about 0.55 cm, about 0.60 cm, about 0.65 cm, or any value or range between any two of these values (including endpoints).

A third high voltage electric potential may be induced between the anode surface and the cathode surface, and the third working fluid may be induced to traverse the gap between the two surfaces. In one non-limiting embodiment, the third high voltage potential may be about 2.4 kV times the gap distance in centimeters to about 60 kV times the gap distance in centimeters, including about 2.4 kV, about 5 kV, about 10 kV, about 20 kV, about 30 kV, about 40 kV, about 50 kV, about 60 kV, or any value or range between any two of these values (including endpoints). In an embodiment, a voltage between the anode surface and the cathode surface (which is 0.3175 cm) is 2.4 kV, thereby resulting in an electrical field of about 7.559 kV/cm. In another non-limiting embodiment, the third high voltage electric potential may be an AC potential having a frequency of about 1 MHz to about 50 MHz, including about 1 MHz, about 5 MHz, about 10 MHz, about 20 MHz, about 25 MHz, about 30 MHz, about 40 MHz, about 50 MHz, or any value or range between any two of these values (including endpoints). In another non-limiting embodiment, the third high-voltage electric potential may have a current of about 100 Amperes to about 1000 Amperes, including about 100 Amperes, about 200 Amperes, about 300 Amperes, about 400 Amperes, about 500 Amperes, about 600 Amperes, about 700 Amperes, about 800 Amperes, about 900 Amperes, about 1000 Amperes, or any value or range between any two of these values (including endpoints).

It may be understood that the anode and cathode surfaces contacting the first working fluid, the second working fluid, and the third working fluid may be the same set of surfaces or they may differ. If each working fluid contacts an independent pair of anode and cathode surfaces, the respective gap distances may be essentially the same or different, and high voltage electric potentials to which the working fluids are exposed may have essentially the same or different characteristics.

It may be appreciated that each source of the high voltage electric fields (generators 110, 115, and 120), such as plasma torches, may be controlled by one or more control systems. Such control systems may be specific for all the plasma torches together and may be different from or included with a control system for the entire power generating system. Alternatively, each plasma torch may have a separate control system. A control system for a plasma torch may include control functions for torch parameters, such as, but not limited to, the value of the high voltage electric fields, and frequency of the high voltage electric fields. Control of the torches may be based on one or more process measurements, including but not limited to, a measurement of a voltage applied to components that may generate the high voltage electric fields, a current drain of a voltage supply for the high voltage electric field generators (110, 115, and 120), such as plasma torches, the temperature of the plasma output of the high voltage electric field generators (110, 115, and 120), and the composition of the plasma in the PPC 125. It may further be appreciated that each of the high voltage electric field generators (110, 115, and 120), as exemplified by plasma torches, may be controlled according to one or more process algorithms. The plasma torches may be controlled according to the same process method or algorithm (as provided by individual controllers or a single controller). Alternatively, each of the plasma torches may be controlled according to a different process method or algorithm (as provided by individual controllers or by a single controller).

In some embodiments, the three working fluids, exemplified by $O_2$, $H_2O$, and $CO_2$, may be combined into one or two combined working fluids before being supplied to one or more high voltage electric field generators (110, 115, or 120). As a non-limiting example, $O_2$, $H_2O$, and $CO_2$ may be combined into a single combined working fluid to be supplied to a single plasma torch. By extension, the controllers associated with each of the supply sources for the $O_2$, $H_2O$, and $CO_2$ may cause a specific amount of each gas to be added to the combined working fluid to produce an optimized ratio of gasses. Similarly, the controller associated with a single plasma torch may cause the plasma torch to operate under optimum conditions for a specific ratio of gasses in the combined working fluid.

The third fluid plasma, the second fluid plasma, and the first fluid plasma together may be directed to contact 240 a carbon source of toxin particulates within the PPC, thereby creating a first fluid mixture and vitrified toxin residue. The carbon source of toxin particulates may be provided 235 from a supply of carbon source of toxin particulates 105. The mechanical components used to transport the carbon source of toxin particulates into the PPC 125 may be controlled according to some process parameters. The control of the transport of the carbon source of toxin particulates may be supplied by a control system. Such a control system may be specific to the mechanical components used to transport the carbon source of toxin particulates into the PPC 125. Alternatively, such a control system may be included in a control system that controls the entire power generation system.

In some non-limiting examples, the PPC 125 may also be maintained at a vacuum or a near vacuum. In one non-limiting example, the PPC 125 may be maintained at a pressure of about 50 kPa (0.5 atmospheres) to about 507 kPa (about 0.5 atmospheres to about 5 atmospheres), including about 50 kPa, about 100 kPa, about 150 kPa, about 200 kPa, about 260 kPa, about 300 kPa, about 350 kPa, about 400 kPa, about 450 kPa, about 500 kPa, about 507 kPa, or any value or range between any two of these values (including endpoints).

The first fluid mixture, while in the PPC 125, may attain temperatures of about 4000° C. to about 20000° C. Higher or lower temperatures may be attained according to the conditions under which the high voltage field generators operate. The first fluid mixture may be cooled within the PPC 125, at an exit port of the PPC, in a transport device (such as a pipe or other duct-work) at an exit of the PPC, or at a combination of these locations through the action of a coolant addition device 128. In one non-limiting example, the coolant may include liquid oxygen (LOX). An amount of coolant introduced into the first fluid mixture by the coolant addition device 128 may be controlled by a control system. In some non-limiting examples, the amount of the coolant added to the first fluid mixture may be controlled according to a temperature of the first fluid mixture, a composition of the first fluid mixture, or other measured parameters of the first fluid mixture. Such a control system may be associated only with the coolant addition device 128. Alternatively, such a control system may be incorporated into a system for controlling the entire power generation system. The addition of the coolant to the first fluid mixture may reduce the temperature of the resulting fluid mixture (an admixed first fluid mixture) to 1450° C. to about 1650° C., including about 1450° C., about 1500° C., about 1550° C., about 1600° C., about 1650° C., or any value or range between any two of these values. It may be further appreciated that the admixed first fluid mixture may have a composition different from that of the first fluid mixture.

Vitrified toxin residue may be removed 245 from the first fluid mixture in the PPC 125 through a residue exit port 126 by various methods. These methods may include vacuum removal, centripetal force resulting in the vitrified toxin residue adhering to the walls of the PPC 125, pumping, draining, gravity flow, or combinations thereof.

The first fluid mixture may be transported 250 to a first heat exchange device 130. In the first heat exchange device 130, the first fluid mixture may exchange at least some heat with a heat exchange material, and thus cool to form a second fluid mixture. In some non-limiting examples, the first heat exchange device 130 may be a first heat recovery steam generator (HRSG). The first heat exchange device 130 may allow transfer of at least some heat from the first fluid mixture to a heat exchange material, such as water. Water may enter the first heat exchange device 130 through a first water input port 129. The amount of water may be controlled by a control system. The heated first heat exchange material, which may include steam as a non-limiting example, may exit the first heat exchange device 130 by means of a first output port 132. The heated first heat exchange material may be further transported to a first electric turbine to generate a first supply of electric power.

In one non-limiting example, the first heat exchange material may be water, which may be converted to a first supply of steam in the first heat exchange device 130. Once the first supply of steam has activated the electric turbine, the first supply of steam may be cooled to liquid water. In some embodiments, the liquid water may be returned to the first heat exchange device 130 to be reheated by more of the first fluid mixture. Alternatively, the first supply of steam, after activating the first electric turbine, may be returned to a working fluid source to be supplied to a high voltage electric field generator (110, 115, or 120), such as one of the plasma torches. In some embodiments, the second working fluid may include an amount of steam generated by the HRSG.

At an output port 132 of the first heat exchange device 130, the second fluid mixture may be cooled 255, resulting in a temperature of about 35° C. to about 1650° C., about 38° C. to about 1620° C., about 60° C. to about 1400° C., about 80° C. to about 1200° C., about 100° C. to about 1000° C., about 200° C. to about 800° C., about 400° C. to about 600° C. The composition of the second fluid mixture may be different from that of the first fluid mixture and that of the admixed first fluid mixture.

The second fluid mixture from the first heat exchange device 130 may be transported 260 to any number of cleaning devices 135 to remove unwanted components, non-limiting examples being sulfur-containing material and mercury-containing materials. Such cleaning devices 135 may include, without limitation, a wet scrubber.

The resultant gas mixture exiting the cleaning devices 135 may include primarily carbon dioxide ($CO_2$) and water ($H_2O$). In some embodiments, such gases may be released into the atmosphere. In other embodiments, the gases may be returned to be re-used at appropriate points in the process. For example, $CO_2$ may be returned to the $CO_2$ supply source while the water may be returned to the water supply source for re-use in the PPC 125.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity. It will be understood by those within the art that, in general, terms used in this disclosure, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this disclosure can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A method of sequestering toxin particulates, the method comprising:

providing a first working fluid;

exposing the first working fluid to a first high voltage electric field to produce a first fluid plasma;

providing a second working fluid;

exposing the second working fluid to a second high voltage electric field to produce a second fluid plasma;

providing a third working fluid;

exposing the third working fluid to a third high voltage electric field to produce a third fluid plasma;

providing an amount of toxin particulates, wherein the toxin particulates comprise one or more binding particulates and the one or more binding particulates include silicates and clays;

contacting the toxin particulates with the third fluid plasma, the second fluid plasma, and the first fluid plasma within a primary processing chamber to form a first fluid mixture and vitrified toxin residue;

removing the vitrified toxin residue;

transporting the first fluid mixture to a first heat exchange device;

cooling the first fluid mixture using the first heat exchange device to form a second fluid mixture; and transporting the second fluid mixture to a wet scrubber.

2. The method of claim 1, wherein the first working fluid is oxygen gas.

3. The method of claim 1, wherein the second working fluid is water vapor.

4. The method of claim 1, wherein the third working fluid is carbon dioxide gas.

5. The method of claim 1, wherein the toxin particulates comprise one or more of the following: pulverized mine tailings and heavy metal particulates.

6. The method of claim 1, wherein exposing the first working fluid to a first high voltage electric field comprises:

providing an anode surface;

providing a cathode surface at a distance from the anode surface, to create a gap between the anode surface and the cathode surface;

providing a first high voltage electric potential between the anode surface and the cathode surface of about 2.4 kV times the distance in centimeters to about 60 kV times the distance in centimeters; and causing the first working fluid to traverse the gap.

7. The method of claim 6, wherein the first high voltage electric potential has a frequency of about 1 MHz to about 50 MHz.

8. The method of claim 1, wherein exposing the second working fluid to a second high voltage electric field comprises:

providing an anode surface;

providing a cathode surface at a distance from the anode surface to create a gap between the anode surface and the cathode surface;

providing a second high voltage electric potential between the anode surface and the cathode surface of about 2.4 kV times the distance in centimeters to about 60 kV times the distance in centimeters; and causing the second working fluid to traverse the gap.

9. The method of claim 8, wherein the second high voltage electric potential has a frequency of about 1 MHz to about 50 MHz.

10. The method of claim 1, wherein exposing the third working fluid to a third high voltage electric field comprises:

providing an anode surface;

providing a cathode surface at a distance from the anode surface to create a gap between the anode surface and the cathode surface;

providing a third high voltage electric potential between the anode surface and the cathode surface of about 2.4 kV times the distance in centimeters to about 60 kV times the distance in centimeters; and causing the third working fluid to traverse the gap.

11. The method of claim 10, wherein the third high voltage electric potential has a frequency of about 1 MHz to about 50 MHz.

12. The method of claim 1, wherein exposing the first working fluid to a first high voltage electric field comprises causing the first working fluid to pass through a first plasma torch.

13. The method of claim 1, wherein exposing the second working fluid to a second high voltage electric field comprises causing the second working fluid to pass through a second plasma torch.

14. The method of claim 1, wherein exposing the third working fluid to a third high voltage electric field comprises causing the third working fluid to pass through a third plasma torch.

15. The method of claim 1, wherein the first fluid mixture has a temperature of about 7230° F. (4000° C.) to about 36000° F. (20000° C.).

16. The method of claim 1, wherein cooling the first fluid mixture comprises cooling the first fluid plasma mixture to a temperature of about 100° F. (38° C.) to about 2950° F. (1620° C.).

17. The method of claim 1, wherein the first heat exchange device is a heat recovery steam generator.

18. The method of claim 17, wherein the second working fluid comprises at least in part an amount of steam generated by the heat recovery steam generator.

19. The method of claim 1, wherein the second fluid mixture further comprises carbon dioxide.

20. The method of claim 19, wherein the third working fluid comprises at least in part an amount of carbon dioxide obtained from the second fluid mixture.

21. The method of claim 1, wherein the second fluid mixture further comprises one or more of the following: toxic material silicates, toxic material carbonates, and vitreous compositions including the toxic materials.

* * * * *